United States Patent
Börnsen et al.

(10) Patent No.: US 7,557,105 B2
(45) Date of Patent: Jul. 7, 2009

(54) N-OXIDES OF N-PHENYL-2-PYRIMIDINE-AMINE DERIVATIVES

(75) Inventors: Klaus Olaf Börnsen, Staufen (DE); Peter End, Oberwil (CH); Gerhard Gross, Lörrach (DE); Ulrike Pfaar, Rheinfelden (DE); Paul William Manley, Arlesheim (CH); Jürg Zimmermann, Binningen (CH)

(73) Assignee: Novartis AG, Basel (CH)

( * ) Notice: Subject to any disclaimer, the term of this patent is extended or adjusted under 35 U.S.C. 154(b) by 330 days.

(21) Appl. No.: 10/502,291

(22) PCT Filed: Jan. 22, 2003

(86) PCT No.: PCT/EP03/00613

§ 371 (c)(1), (2), (4) Date: Apr. 29, 2005

(87) PCT Pub. No.: WO03/062220

PCT Pub. Date: Jul. 31, 2003

(65) Prior Publication Data

US 2005/0209452 A1    Sep. 22, 2005

(30) Foreign Application Priority Data

Jan. 23, 2002   (GB)   ................... 0201508.9

(51) Int. Cl.
  *C07D 401/14*   (2006.01)
  *A61K 31/506*   (2006.01)

(52) U.S. Cl. .................. 514/252.18; 544/295
(58) Field of Classification Search ................ 544/295; 514/252.18
See application file for complete search history.

(56) References Cited

U.S. PATENT DOCUMENTS 5,521,184 A     5/1996   Zimmermann
7,279,576 B2 *  10/2007  Flynn et al. ................. 544/322

FOREIGN PATENT DOCUMENTS

| WO | WO 99/03854 | 1/1999 |
| WO | 00 78731 | 12/2000 |
| WO | 02 22597 | 3/2002 |

OTHER PUBLICATIONS

Traxler, Protein Tyrosine Kinase inhibitors in cancer treatment, Exp. Opin. Ther. Patents, 7(6):571-588, 1997.*
Simone, Oncology; Introduction, Cecil Textbook of Medicine, 20th Edition, vol. 1, pp. 1004-1010, 1996.*

* cited by examiner

*Primary Examiner*—Deepak Rao
(74) *Attorney, Agent, or Firm*—George R. Dohmann

(57) ABSTRACT

The invention relates to N-phenyl-2-pyrimidine-amine derivatives in which at least one nitrogen atom carries an oxygen atom to form the corresponding N-oxides, to processes for the preparation thereof, to pharmaceutical compositions comprising those compounds, and to the use thereof in the preparation of pharmaceutical compositions for the therapeutic treatment of warm-blooded animals, including humans.

5 Claims, No Drawings

N-OXIDES OF N-PHENYL-2-PYRIMIDINE-AMINE DERIVATIVES

This application is a 371 of PCT/EP03/00613 filed Jan. 22, 2003.

The invention relates to N-phenyl-2-pyrimidine-amine derivatives in which at least one nitrogen atom carries an oxygen atom to form the corresponding N-oxides, to processes for the preparation thereof, to pharmaceutical compositions comprising those compounds, and to the use thereof in the preparation of pharmaceutical compositions for the therapeutic treatment of warm-blooded animals, including humans.

The invention relates particularly to compounds of formula I

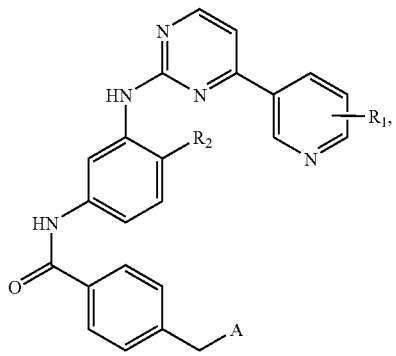

wherein
$R_1$ is hydrogen or hydroxy,
$R_2$ is hydrogen, lower alkyl or hydroxy-lower alkyl,
A is —$NR_5R_6$, —$CR_5R_6$ or —$OR_5R_6$,
$R_5R_6$ together represent alkylene with four, five or six carbon atoms, oxa-lower alkylene with one oxygen and three or four carbon atoms, or aza-lower alkylene with one or two nitrogen and two, three or four carbon atoms wherein the nitrogen atom is unsubstituted or substituted by lower alkyl, hydroxy-lower alkyl, or acetyl, and wherein lower alkylene in each case may be partially or totally unsaturated and/or the carbon atoms of lower alkylene may be substituted by lower alkyl, hydroxyl, lower alkoxy or oxo when lower alkylene is not totally unsaturated, and wherein at least one nitrogen atom carries an oxygen atom to form the corresponding N-oxide or when no nitrogen atom carries an oxygen atom, A is substituted by oxo on a ring carbon, or a pharmaceutically acceptable salt of such a compound.

Preferably A is substituted by oxo on a ring carbon.

Preferably A is pyrrolidino, piperidyl, piperidino, piperazinyl, pyridyl, pyrrolidino, pyrrolidinyl, morpholino, lower alkylpiperazino, N-methylpiperazino, 4-methyl-3-oxo-1-piperazinyl, 3-oxo-1-piperazinyl, 1H-imidazolyl, 1H-2-methylimidazolyl, 1H-4-methylimidazolyl or 1H-2,4-dimethylimidazolyl, cyclohexyl or phenyl, optionally substituted by oxo on a ring carbon;

Most preferably "A" represents a piperazino group of the following formula A'

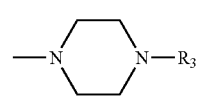

wherein
$R_3$ represents, hydrogen, lower alkyl or acetyl.

Preference is given to compounds of formula I, wherein
$R_1$ is hydrogen,
$R_2$ is hydrogen, methyl or hydroxymethyl,
A is A', optionally substituted by oxo on a ring carbon,
$R_3$ is methyl or hydrogen, or salts of such compounds.

When "A" is substituted by oxo on a ring carbon, "A" is preferably selected from lower alkyl-oxo-piperazino such as 4-methyl-3-oxo-1-piperazinyl or oxo-piperazino such as 3-oxo-1-piperazinyl, oxo-pyrrolidin, oxo-piperidino, oxo-piperidyl, oxo-morpholino, oxo-cyclohexyl, succinimido or glutarimido.

The nitrogen atoms, which carry an oxygen atom to form the corresponding N-oxides are preferably the ring nitrogen atoms located on pyrimidine, pyrindinyl, "A" or piperazino group of the formula A'.

By defining "$R_5R_6$ together", the applicant does not include in the numbering the nitrogen, oxygen or carbon group mentioned in $NR_5R_6$, $CR_5R_6$ or $OR_5R_6$.

The prefix "lower" denotes a radical having up to and including a maximum of 7, especially up to and including a maximum of 4 carbon atoms, the radicals in question being either linear or branched with single or multiple branching.

Lower alkyl is preferably alkyl with from and including 1 up to and including 7, preferably from and including 1 to and including 4, and is linear or branched; preferably, lower alkyl is butyl, such as n-butyl, sec-butyl, isobutyl, tert-butyl, propyl, such as n-propyl or isopropyl, ethyl or methyl. Preferably lower alkyl is methyl, propyl or tert-butyl.

Hydroxy-lower alkyl, preferably hydroxymethyl, 2-hydroxyethyl or 2-hydroxy-2-propyl.

Lower alkoxy is especially methoxy, ethoxy, isopropyloxy, or tert-butyloxy.

In a preferred aspect, the invention relates to compounds of formula II

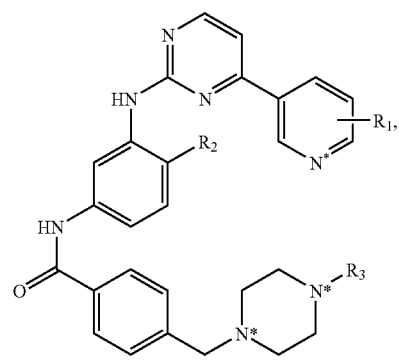

wherein

R₁ is hydrogen or hydroxy,

R₂ is lower alkyl or hydroxy-lower alkyl,

R₃ is hydrogen, methyl or acetyl, and the stars indicate the nitrogen atoms which optionally carry an oxygen atom to form the corresponding N-oxides, with the proviso that at least one of the three nitrogen atoms marked by a star carries an oxygen atom if $R_1$ is hydrogen, $R_2$ is methyl and $R_3$ is hydrogen or methyl, or salts of such compounds.

Optionally, the nitrogen atoms of the 2-pyrimidine can also carry one or two oxygen atoms to form the corresponding N-oxides.

Preferably, a compound of formula II carries at least one oxygen atom to form the corresponding N-oxide.

Optionally, the piperazinyl is substituted by oxo to from a lower alkyl-oxo-piperazino such as 4-methyl-3-oxo-1-piperazinyl or an oxo-piperazino such as 3-oxo-1-piperazinyl.

The term "lower" within the scope of compounds of formula II denotes radicals having up to and including 7, preferably up to and including 4 carbon atoms.

When $R_1$ is hydroxy, the 3-pyridinyl moiety is substituted by hydroxy at a ring carbon atom at position 2, 4, 5 or 6.

Lower alkyl $R_2$ is preferably methyl.

Hydroxy-lower alkyl $R_2$ is preferably hydroxymethyl.

Salts are especially the pharmaceutically acceptable salts of compounds of formula I or II.

Such salts are formed, for example, as acid addition salts, preferably with organic or inorganic acids, from compounds of formula I or II with a basic nitrogen atom, especially the pharmaceutically acceptable salts.

For isolation or purification purposes it is also possible to use pharmaceutically unacceptable salts, for example picrates or perchlorates. Only the pharmaceutically acceptable salts or free compounds (if the occasion arises, in the form of pharmaceutical compositions) attain therapeutic use, and these are therefore preferred.

In view of the close relationship between the novel compounds in free form and in the form of their salts, including those salts that can be used as intermediates, for example in the purification or identification of the novel compounds, hereinbefore and hereinafter any reference to the free compounds is to be understood as referring also to the corresponding salts, as appropriate and expedient.

A compound of formula I or II possesses valuable pharmacological properties and may, for example, be used as an anti-tumour agent, as an agent to treat atherosclerosis, as an agent to treat restenosis, as an anti-leukemic agent for the prevention of transplantation-induced disorders, such as obliterative bronchiolitis, and/or for preventing the invasion of warm-blooded animal cells by certain bacteria, such as *Porphyromonas gingivalis*.

The phosphorylation of proteins has long been known as an essential step in the differentiation and division of cells. Phosphorylation is catalysed by protein kinases subdivided into serine/threonine and tyrosine kinases. The tyrosine kinases include PDGF (Platelet-derived Growth Factor) receptor tyrosine kinase.

PDGF is a very commonly occurring growth factor, which plays an important role both in normal growth and also in pathological cell proliferation, such as is seen in carcinogenesis and in diseases of the smooth-muscle cells of blood vessels, for example in atherosclerosis and thrombosis.

The inhibition of PDGF-stimulated receptor tyrosine kinase activity in vitro is measured in PDGF receptor immune complexes of A431 cells, as described by E. Andrejauskas-Buchdunger and U. Regenass in Cancer Research 52, 5353-5358 (1992). A compound of formula I or II inhibits PDGF-dependent acellular receptor phosphorylation. The inhibition of PDGF receptor tyrosine kinase is measured in a microtitre ELISA assay (cf Trinks et al., J. Med. Chem. 37, 1015-27 (1994).

The inhibition of PDGF receptor tyrosine kinase makes a compound of formula I or II also suitable for the treatment of tumour diseases, such as gliomas, sarcomas, prostate tumours, and tumours of the colon, breast, and ovary.

A compound of formula I or II also inhibits cellular processes involving the so-called stem-cell factor (SCF, also known as the c-Kit ligand or steel factor), such as SCF receptor (Kit) autophosphorylation and the SCF-stimulated activation of MAPK kinase (mitogen-activated protein kinase).

In particular, a compound of formula I or II inhibits the tyrosine kinase activity of c-Kit. This can be shown in a tyrosine kinase inhibition assay using the cytoplasmatic kinase domain of c-Kit. The assay is performed as follows: The baculovirus donor vector pFbacG01 (GIBCO) is used to generate a recombinant baculovirus that expresses the amino acid region amino acids 544-976 of the cytoplasmic kinase domains of human c-Kit. The coding sequences for the cytoplasmic domain of c-Kit is amplified by PCR from a human uterus c-DNA library (Clontech). The amplified DNA fragment and the pFbacG01 vector are made compatible for ligation by digestion with BamHI and EcoRI. Ligation of these DNA fragments results in the baculovirus donor plasmid c-Kit. The production of the viruses, the expression of proteins in Sf9 cells and the purification of the GST-fused proteins are performed as follows:

Production of virus: Transfer vector (pFbacG01-c-Kit) containing the c-Kit kinase domain is transfected into the DH10Bac cell line (GIBCO) and the transfected cells are plated on selective agar plates. Colonies without insertion of the fusion sequence into the viral genome (carried by the bacteria) are blue. Single white colonies are picked and viral DNA (bacmid) is isolated from the bacteria by standard plasmid purification procedures. Sf9 cells or Sf21 cells (American Type Culture Collection) are then transfected in 25 cm² flasks with the viral DNA using Cellfectin reagent.

Determination of small scale protein expression in Sf9 cells: Virus containing media is collected from the transfected cell culture and used for infection to increase its titre. Virus containing media obtained after two rounds of infection is used for large-scale protein expression. For large-scale protein expression 100 cm² round tissue culture plates are seeded with $5 \times 10^7$ cells/plate and infected with 1 mL of virus-containing media (approx. 5 MOIs). After 3 days the cells are scraped off the plate and centrifuged at 500 rpm for 5 min. Cell pellets from 10-20, 100 cm² plates, are resuspended in 50 mL of ice-cold lysis buffer (25 mM Tris-HCl, pH 7.5, 2 mM EDTA, 1% NP-40, 1 mM DTT, 1 mM PMSF). The cells are stirred on ice for 15 min and then centrifuged at 5000 rpms for 20 min.

Purification of GST-tagged protein: The centrifuged cell lysate is loaded onto a 2 mL glutathione-sepharose column (Pharmacia) and washed three times with 10 mL of 25 mM Tris-HCl, pH 7.5, 2 mM EDTA, 1 mM DTT, 200 mM NaCl. The GST-tagged protein is eluted by 10 applications (1 mL each) of 25 mM Tris-HCl, pH 7.5, 10 mM reduced-glutathione, 100 mM NaCl, 1 mM DTT, 10% Glycerol and stored at −70° C.

Kinase assay: Tyrosine protein kinase assays with purified GST-c-Kit are carried out in a final volume of 30 μL containing 200-1800 ng of enzyme protein (depending on the specific activity), 20 mM Tris-HCl, pH 7.6, 3 mM $MnCl_2$, 3 mM MgCl$_2$, 1 mM DTT, 10 μM Na$_3$VO$_4$, 5 μg/mL poly(Glu,Tyr) 4:1, 1% DMSO, 1.0 μM ATP and 0.1 μCi [γ$^{33}$P] ATP. The activity is assayed in the presence or absence of inhibitors, by measuring the incorporation of $^{33}$P from [γ$^{33}$P] ATP into the poly(Glu,Tyr) 4:1 substrate. The assay (30 μL) is carried out in 96-well plates at ambient temperature for 20 min under conditions described below and terminated by the addition of 20 μL of 125 mM EDTA. Subsequently, 40 μL of the reaction mixture is transferred onto Immobilon-PVDF membrane (Millipore, Bedford, Mass., USA) previously soaked for 5 min with methanol, rinsed with water, then soaked for 5 min with 0.5% H$_3$PO$_4$ and mounted on vacuum manifold with disconnected vacuum source. After spotting all samples, vacuum is connected and each well rinsed with 200 μL 0.5% H$_3$PO$_4$. Membranes are removed and washed 4× on a shaker with 1.0% H$_3$PO$_4$ and once with ethanol.

Membranes are counted after drying at ambient temperature, mounting in Packard TopCount 96-well frame, and addition of 10 μwell of Microscint™ (Packard). IC$_{50}$ values are calculated by linear regression analysis of the percentage inhibition of each compound in duplicate, at four concentrations (usually 0.01, 0.1, 1 and 10 μM). One unit of protein kinase activity is defined as 1 nmole of $^{33}$P ATP transferred from [γ$^{33}$P] ATP to the substrate protein per minute per mg of protein at 37° C.

A compound of formula I or II inhibits also the autophosphorylation of SCF receptor (and c-Kit, a proto-oncogen). Inhibition of the autophosphorylation of the SCF receptor can be measured using e.g. MO7e cells, a human promegakaryocytic leukaemia cell line which depends on SCF for proliferation. They are obtained from Grover Bagby, Oregon Health Sciences University, USA. The cells are cultivated in RPMI 1649 medium supplemented with 10 FBS and 2.5 ng/ml GC-CMF. GM-SCF and SCF are commercially available. Serum-deprived MO7e cells are prepared and incubated for 90 min at 37° C. with the test substance before being stimulated with recombinant SCF for 10 min at 37° C. Identical quantities of cell lysates are analysed by Western blot using antiphosphotyrosine antibodies (Buchdunger et al., Proc. Natl. Acad. Sci (USA) 92, 2558-62 (1995)). The immunodecorated proteins are detected by means of the ECL Western blotting system from Amersham (Amersham, UK).

On the basis of the described properties, a compound of formula I or II may be used not only as a tumour-inhibiting substance, for example in small cell lung cancer, but also as an agent to treat non-malignant proliferative disorders, such as atherosclerosis, thrombosis, psoriasis, scieroderma, and fibrosis, as well as for the protection of stem cells, for example to combat the haemotoxic effect of chemotherapeutic agents, such as 5-fluoruracil, and in asthma. It may especially be used for the treatment of diseases which respond to an inhibition of the PDGF receptor kinase.

In addition, a compound of formula I or II prevents the development of multidrug resistance in cancer therapy with other chemotherapeutic agents or abolishes a pre-existing resistance to other chemotherapeutic agents. Also regardless of the effect described hereinbefore, a compound of formula I or II may be used to advantage in combination with other antitumour agents, such as especially other c-Kit inhibitors and inhibitors of Vascular Endothelial Growth Factor (VEGF) receptor or c-Src activity.

Also Abl kinase, especially v-Abl kinase, is inhibited by a compound of formula I or II. The inhibition of v-Abl tyrosine kinase is determined by the methods of N. Lydon et al., Oncogene Research 5, 161-173 (1990) and J. F. Geissler et al., Cancer Research 52, 4492-8 (1992). In those methods [Val$^5$]-angiotensin II and [γ-$^{32}$P]-ATP are used as substrates.

By analogy, a compound of formula I or II also inhibits Bcr-Abl kinase (see Nature Medicine 2, 561-566 (1996)) and is thus suitable for the treatment of Bcr-Abl-positive cancer and tumour diseases, such as leukaemias (especially chronic myeloid leukaemia and acute lymphoblastic leukaemia, where especially apoptotic mechanisms of action are found), and also shows effects on the subgroup of leukaemic stem cells as well as potential for the purification of these cells in vitro after removal of said cells (for example, bone marrow removal) and reimplantation of the cells once they have been cleared of cancer cells (for example, reimplantation of purified bone marrow cells).

Test for activity against c-Abl protein tyrosine kinase. The test is conducted as a filter binding assay as follows: The His-tagged kinase domain of c-Abl is cloned and expressed in the baculovirus/Sf9 system as described by Bhat et al., J. Biol. Chem. 272, 16170-5 (1997). A protein of 37 kD (c-Abl kinase) is purified by a two-step procedure over a cobalt metal chelate column followed by an anion exchange column with a yield of 1-2 mg/L of Sf9 cells.

The purity of the c-Abl kinase is >90% as judged by SDS-PAGE after Coomassie blue staining. The assay contains: c-Abl kinase (50 ng), 20 mM Tris-HCl, pH 7.5, 10 mM MgCl$_2$, 10 μM Na$_3$VO$_4$, 1 mM DTT and 0.06 μCi/assay [γ$^{33}$P]-ATP (5 μM ATP) using 30 μg/mL poly-Ala,Glu,Lys,Tyr-6:2:5:1 (Poly-AEKY, Sigma P1152) in the presence of 1% DMSO, total volume of 30 μL. Reactions are terminated by adding 10 μL of 250 mM EDTA, and 30 μL of the reaction mixture is transferred onto Immobilon-PVDF membrane (Millipore, Bedford, Mass., USA) previously soaked for 5 min with methanol, rinsed with water, then soaked for 5 min with 0.5% H$_3$PO$_4$ and mounted on vacuum manifold with disconnected vacuum source. After spotting all samples, vacuum is connected and each well rinsed with 200 μL 0.5% H$_3$PO$_4$. Membranes are removed and washed on a shaker with 0.5% H$_3$PO$_4$ (4 times) and once with ethanol. Membranes are counted after drying at ambient temperature, mounting In Packard TopCount 96-well frame, and addition of 10 μL/well of Microscint™ (Packard).

Test for activity against Bcr-Abl. The murine myeloid progenitor cell line 32Dcl3 transfected with the p210 Bcr-Abl expression vector pGDp210Bcr/Abl (32D-bcr/abl) was obtained from J. Griffin (Dana Faber Cancer Institute, Boston, Mass., USA). The cells express the fusion Bcr-Abl protein with a constitutively active Abl kinase and proliferate growth factor independent. The cells are expanded in RPMI 1640 (AMIMED), 10% fetal calf serum, 2 mM glutamine (Gibco) ("complete medium"), and a working stock is prepared by freezing aliquots of 2×10$^6$ cells per vial in freezing medium (95% FCS, 5% DMSO (SIGMA)). After thawing, the cells are used during maximally 10-12 passages for the experiments.

For cellular assays, compounds are dissolved in DMSO and diluted with complete medium to yield a starting concentration of 10 μM followed by preparation of serial 3-fold dilutions in complete medium. 200'000 32D-Bcr/Abl cells in 50 μL complete medium are seeded per well in 96 well round bottom tissue culture plates. 50 μL per well of serial 3-fold dilutions of the test compound are added to the cells in triplicates. Untreated cells are used as control. The compound is incubated together with the cells for 90 min at 37° C., 5% CO$_2$, followed by centrifugation of the tissue culture plates at 1300 rpm (Beckman GPR centrifuge) and removal of the supernatants by careful aspiration taking care not to remove any of the pelleted cells. The cell pellets are lysed by addition of 150 μL lysis buffer (50 mM Tris/HCl, pH 7.4, 150 mM sodium chloride, 5 mM EDTA, 1 mM EGTA, 1% NP-40, 2 mM sodium ortho-vanadate, 1 mM PMSF, 50 µg/mL aprotinin and 80 µg/mL leupeptin) and either used immediately for the ELISA or stored frozen in the plates at −20° C. until usage.

Black ELISA plates (Packard HTRF-96 black plates) are precoated over night at 4° C. with 50 ng/well of the rabbit polyclonal anti-abl-SH3 domain Ab 06-466 from Upstate in 50 µL PBS. After washing 3 times with 200 µL/well PBS containing 0.05% Tween20 (PBST) and 0.5% TopBlock (Juro), residual protein binding sites are blocked with 200 µL/well PBST, 3% TopBlock for 4 h at room temperature followed by incubation with 50 µL lysates of untreated or compound-treated cells (20 µg total protein per well) for 3-4 h at 4° C. After 3 washings, 50 µL/well anti-phosphotyrosine Ab PY20(AP) labeled with alkaline phosphatase (Zymed) diluted to 0.2 µg/mL in blocking buffer is added and incubated over night (4° C.). For all incubation steps the plates are covered with plate sealers (Costar). Finally, the plates are washed another three times with washing buffer and once with deionized water before addition of 90 pL/well of the AP-substrate CDPStar RTU with Emerald II. The plates, now sealed with Packard TopSeal™-A plate sealers, are incubated for 45 min at room temperature in the dark and luminescence is quantified by measuring counts per second (CPS) with a Packard Top Count Microplate Scintillation Counter (Top Count). The difference between the ELISA-readout (CPS) obtained for with the lysates of the untreated 32D-Bcr/Abl cells and the readout for the assay-background (all components, but without cell lysate) is calculated and taken as 100% reflecting the constitutively phosphorylated Bcr-Abl protein present in these cells. The activity of the compound on the Bcr-Abl kinase activity is expressed as percent reduction of the Bcr-Abl phosphorylation. The values for the $IC_{50}$ and $IC_{90}$ are determined from the dose response curves by graphical extrapolation.

Test for activity against mutant Bcr-Abl: The activity of compounds on the M351T mutant Bcr-Abl kinase activity is assessed as described above, except that 32Dcl3 cells transfected with mutant Bcr-Abl in place of p210 Bcr-Abl are utilised.

c-Raf-1 protein kinase assay: Recombinant c-Raf-1 protein is obtained by triple infection of Sf21 cells with GST-c-Raf-1 recombinant baculovirus together with v-Src and v-Ras recombinant baculoviruses that are required for active c-Raf-1 kinase production (Williams et al., PNAS 1992; 89:2922-6). Active Ras (v-Ras) is required to recruit c-Raf-1 to the cell membrane and v-Src to phosphorylate c-Raf-1 to fully activate it. Cells are seeded at $2.5 \times 10^7$ cells per 150 mm dish and allowed to attach to a 150 mm dish for 1 hr at RT. Media (SF900II containing 10% FBS) is aspirated and recombinant baculovirus GST-c-Raf-1, v-Ras and v-Src are added at MOI of 3.0, 2.5 and 2.5, respectively, in a total volume of 4-5 mL. Cells are incubated for 1 hr at RT and then 15 mL of medium is added. Infected cells are incubated for 48-72 hr at 27° C. Infected Sf21 cells are scraped and collected into a 50 mL tube and centrifuged for 10 min at 4° C. at 1100 g in a Sorvall centrifuge. The cell pellet is washed once with ice cold PBS and lysed with 0.6 mL lysis buffer per $2.5 \times 10^7$ cells. Complete lysis of cells is achieved after 10 min on ice with occasional pipetting. The cell lysates are centrifuged for 10 min at 4° C. at 14,500 g in a Sorvall centrifuge with SS-34 rotor and the supernatant is transferred to a fresh tube and stored at −80° C. c-Raf-1 is purified from cell lysates using 100 µL of packed glutathione-sepharose 4B beads equilibrated in ice cold PBS per $2.5 \times 10^7$ cells. GST-c-Raf-1 is allowed to bind to the beads at 4° C. for 1 hr with rocking. Bound GST-c-Raf-1 with beads is transferred to a column. The column is washed once with lysis buffer and twice with ice cold Tris buffered saline. Ice cold elution buffer is added and column flow is stopped to allow the free glutathione to disrupt the interaction of GST-c-Raf-1 with glutathione sepharose beads. Fractions (1 mL) are collected into prechilled tubes. Each tube contains 10% glycerol (final concentration) to maintain kinase activity during freeze thaw cycles. Purified fractions of GST-c-Raf-1 kinase protein are stored at −80° C.

IκB is used as substrate for the c-Raf-1 kinase. IκB is expressed in bacteria as a His-tagged protein BL21. LysS bacteria containing the IκB plasmid are grown to an OD600 of 0.6 in LB medium, then induced to express the IκB with IPTG (final concentration of 1 mM) for 3 hrs at 37° C. and then bacteria are lysed by sonication (microtip limit setting for 3 times at 1 min each in sonication buffer [50 mM Tris pH 8.0, 1 mM DTT, 1 mM EDTA] and centrifuged at 10,000 g for 15 min. The supernatant is mixed with ammonium sulfate to give a final concentration of 30%. This mixture is rocked for 15 min at 4 C then spun at 10,000 g for 15 min. The pellet is resuspended in binding buffer (Novagen) containing 10 mM BSA. This solution is applied to Ni-agarose (Novagen) and washed according to the Novagen manual. IκB is eluted from the column using elution buffer (0.4 M imidazole, 0.2 M NaCl, 8 mM Tris pH 7.9). Fractions containing protein are dialysed in 50 mM Tris pH 8, 1 mM DTT.

The activity of c-Raf-1 protein kinase is assayed in the presence or absence of inhibitors, by measuring the incorporation of $^{33}P$ from [y33p] ATP into IκB. The assay is carried out in 96-well plates at ambient temperature for 60 min. It contains (total volume of 30 µL): c-Raf-1 kinase (400 ng), 25 mM Tris-HCl, pH 7.5, 5 mM $MgCl_2$, 5 mM $MnCl_2$, 10 µM $Na_3VO_4$, 1 mM DTT and 0.3 µCi/assay [y33 P]-ATP (10 µM ATP) using 600 ng IκB in the presence of 1% DMSO. Reactions are terminated by adding 10 µL of 250 mM EDTA and 30 µL of the reaction mixture is transferred onto lmmobilon-PVDF membrane (Millipore, Bedford, Mass., USA) previously soaked for 5 min with methanol, rinsed with water, then soaked for 5 min with 0.5% $H_3PO_4$ and mounted on vacuum manifold with disconnected vacuum source. After spotting all samples, vacuum is connected and each well rinsed with 200 µL 0.5% $H_3PO_4$. Membranes are removed and washed 4× on a shaker with 0.5% $H_3PO_4$, once with ethanol. Membranes are counted after drying at ambient temperature, mounting in Packard TopCount 96-well frame, and addition of 10 µL/well of Microscint™ (Packard).

It has also been surprisingly discovered that our compounds of formula I or II have an unexpected potential to serve as hypoxia-selective products due to bio-reduction (deoxygenation) in the cell especially in the tumours and in the brain. Hypoxia-activated pro-drugs are especially useful in cancer therapy since severe hypoxia occurs in solid tumour tissue or in the brain. Hypoxic cells can be exploited for therapy by non-toxic, hypoxia-activated pro-drugs. Thus because of the net reduction of the N-oxide moiety, there is an higher uptake of compounds of formula I or II in the tumours or in the brain and an accumulation of the reduced form of the compounds of formula I or II in the tumours or brain.

Another advantage of the compounds of formula I or II, is superior effects to carrier-mediated efflux over compound A (by a saturable system, probably P-gp). Consequences of this less pronounced efflux is;

a greater absorption higher drug levels in the brain and higher drug levels in the tumour.

This effect on P-gp and transport mechanism may be demonstrated as follows:

Caco-2 cell monolayers grown on polyethylene terephthalate (PET) filters (Falcon™) for 21-25 days are used for transport experiments. The flux of compounds across Caco-2 cell monolayers grown on PET filters as well as across PET filters alone without Caco-2 cells (for system validation) in the presence and absence of the potent efflux pump inhibitors CsA and Verapamil, respectively, are determined as follows: Prior to the transport experiment, the culture medium in the acceptor compartment (0.2 ml for apical and 1.0 ml for basolateral sides) is replaced with acceptor solution (HBSS, when relevant containing the inhibitor of interest) preincubated at 37° C. To start the experiment, the medium in the donor compartment (0.35 ml for apical and 1.15 ml for basolateral sides) is replaced with donor solution (compound in HBSS, when relevant containing inhibitor of interest) preincubated at 37° C. Aliquots of 150 µl are removed from the donor and the acceptor side after about 1 and 120 minutes. Transport experiments in both apical-to-basolateral and basolateral-to-apical directions are performed in triplicate at 37° C. in an incubator without shaking.

Furthermore, the plasma protein binding of the compounds of formula I or II is superior with regard to free fraction and/or association with plasma proteins (e.g. albumin, α-1-acid glycoprotein (MG)), to that observed with compound A. A lower extent of association to MG results in less pronounced variability of free fraction of N-oxides and also has an effect of free fraction of compound A compounds. At the clinically relevant dose of 400 mg daily dose (concentrations of 900-2600 ng/mL of compound A), the free fraction of compound A ranges from 4 to 5%. Using erythrocyte partitioning, compound A was mainly found associated with albumin and alpha-1-acid glycoprotein (MG). The fraction associated with lipoproteins and gamma globulins was <5%. The reduced plasma protein-binding of compounds of formula I or II is shown by the following example.

The free (or unbound) fraction of compounds of formula I or II is determined by the ultracentrifugation method which was used also for compound A (see European patent application No. 1250140 or International patent application WO 01/47507 filed on Dec. 22, 2000). Solutions of human serum albumin (40 g/L) and α-1-acid glycoprotein (1 g/L) will be prepared in Soerensen buffer pH 7.4 containing 0.9% NaCl (w/v). 30 µL of the compounds of formula I or II stock solutions are directly spiked into 3 mL of the protein solutions to get the intended final concentrations of 300-5000 ng/mL compounds of formula I or II (ethanol final concentration 0.5%, factor 1:200). After incubation for 30 min at 37° C. under constant gentle agitation, the spiked protein samples (n=3/4) are centrifuged at 200'000 g for at least 5 hours h at 37° C. (centrifuge with a fixed angle rotor) using thick-walled polycarbonate centrifuge tubes. The spin is stopped without braking. The concentration of compounds of formula I or II are determined after incubation (before centrifugation) and after centrifugation in the supernatant.

The pharmacokinetics of the compounds of formula I or II are advantageous over compound A with regard to $C_{max}$ (highest observed concentration in plasma in units mass/volume), half-live (refers to the time after administration of the drug to observe a diminution of one half of the measured pharmacological response; In one aspect, the half-life is enhanced when the half-life is increased by at least 50%) or AUC (plasma concentrations over time, as defined by the Area Under the Curve (AUC) in units of mass-time/volume) in plasma as a matter of transport mechanism (e.g. P-gp). This advantageous pharmacokinetics is shown by giving to animals (e.g. rats) a single dose of compounds of formula I or II (one group of animals will be treated intravenously and one group of animals will be treated per orally). Blood is taken at selected time points (e.g. 0.083 min (iv: intra venous) and 0.25, 0.5, 1, 2, 4, 6, 8, 10, 12, 24 and 48 h after iv or po (per orally dosing). Plasma is prepared immediately by centrifugation of blood. Unchanged compounds of formula I or II and compound A are measured in plasma using HPLC/UV detection or LC-MS.

Furthermore, the reduced plasma protein binding of the compounds of formula I or II to plasma proteins can cause an increase in the apparent volume of distribution due to higher fraction of unbound drug (fu). Advantageously, the distribution of the compounds of formula I or II into organs and tissues (including the brain) is different from that of compound A. This can be shown as follows.

Compounds of formula I or II and compound A in brain of mice or rats upon dosing with non-radiolabelled N-oxide.

Animals (e.g. mice or rats) receive a single dose of compounds of formula I or II (one group of animals is treated intravenously and one group of animals is treated per orally). Animals are sacrificed at selected time points (e.g. 0.083 min (iv) and 1, 8, 24 and 48 h after iv or po dosing). Brain of treated animals are taken, homogenates of brain are prepared and samples are prepared (e.g. extraction of homogenate with organic solvent such as methanol, acetonitrile or others) for analysis (HPLC/UV or LC-MS) of compounds of formula I or II and compound A. Concentrations of compounds of formula I or II and compound A in brain and plasma is measured for determination of ratio brain/plasma.

Distribution of radioactive substance(s) in mice or rats upon dosing with radiolabelled N-oxide.

For the tissue distribution study, e.g. 10 mg/kg po of radiolabelled N-oxide (e.g. [$^{14}$C]-label; 100 µCi/kg b.w.) is administered to animals. The uptake/distribution of radioactive substance(s) throughout the body of the animal is investigated using quantitative whole-body autoradioluminography (QW-ABL). The animals are sacrificed at selected time points and frozen in a mixture of dry-ice and hexane at approx. −75° C. Frozen animals are embedded in a pre-cooled 2% aqueous gel of Na-CMC, at approx. −75° C.; 40 µm thick sections are obtained at ca. −20° C. in a CryoMacrocut cryomicrotome (Leica Instr. GmbH, D-Nussloch). Dehydration of sections take place during 24-60 h at −23° C. in the cryomicrotome. Sections exposure to BAS III Imaging plates (Fuji Photo Film Co., Ltd., J-Tokyo) for 1 day at room temperature in a lead shielding box to minimize the increase of the background. The duration of exposure allows detection of ca. 2 dpm/mg, i.e. the radioactivity concentration corresponding to ca. 0.2-0.4% of the total radioactive dose if the radioactivity was evenly distributed throughout the body. Scan is performed in a Fuji BAS 2000 TR phosphor imager, immediately after the end of the exposure, under controlled light conditions, at a 100 µm scanning step with a 1024 gradation. Image analysis is done as follows: The resulting photostimulated light data files are corrected by subtracting the background, processed electronically with the help of a MCID/M4 (3.0 Rev. 1.3) image analyzer (Imaging Research, St. Catherines, Ontario, Canada) and automatically converted into radioactivity concentrations using a 1st degree polynomial calibration curve obtained from a radioactive blood scale processed under similar conditions as the samples. Detection (LD) and quantitation (QL) limits are determined by LD=mean of background (n=10)+3 SD; QL=3 LD.

The size of the measurement areas are the same as that of each blood standard of the blood scale used to set the calibration curve. Image files processed using the Adobe Photoshop® software.

For distribution of total radioactive substance(s) Using QWABL only half of the treated animal are used which makes possible to use organs or tissues for determination of unchanged N-oxide and/or compound A in selected samples using HPLC/UV or HPLC-radioactivity and/or LC-MS.

Compounds of formula I or II have also less affinity to CYP450s [1, 2], because of N-oxides which are more polar. These enzymes are metabolizing most of the drugs on the market. Less affinity translates to smaller drug/drug interaction potential. Especially the blocking of a basic nitrogen like in a piperazine/pyridine moiety reduce the affinity to CYP2D6 an enzyme which binds substrates especially by ionic interaction with the aspartate residue which requires a basic moiety like the nitrogen in the piperazine ring system. A pool out of ten different human liver microsomes are incubated with all cofactors necessary for their metabolic activity (NADPH) with defined marker substrates for the respective CYP450 isozyme specific activity. The potential inhibitor is added with increasing concentrations and the metabolic reactions are evaluated by the corresponding analytical method (LC/MS, HPLC, Fluorescence). The conversion rate without inhibitor is set to 100% and the inhibition rate is evaluated as the concentration of inhibitor needed to suppress 50% of the conversion (IC50). The following marker substrates are used:

| CYP | Substrates Preferred | Acceptable |
|---|---|---|
| 1A2 | Ethoxyresorufin Phenacetin | Caffeine (low turnover) Theophylline (low turnover) Acetanilide (mostly applied in hepatocytes) Methoxyresorufin |
| 2A6 | Coumarin | |
| 2C8 | Paclitaxel (availability of standards?) | |
| 2C9 | S-Warfarin Diclofenac | Tolbutamide (low turnover) |
| 2C19 | S-Mephenytoin (4-hydroxy metabolite) Omeprazole | |
| 2D6 | Bufuralol Dextromethorphan | Metoprolol Debrisoquine Codeine (all with no problems, but less commonly used) |
| 2E1 | Chlorzoxazone | 4-Nitrophenol Lauric Acid |
| 3A4 | Midazolam Testosterone (strongly recommended to use at least two structurally unrelated substrates) | Nifedipine Felodipine Cyclosporin Terfenadine Erythromycin Simvastatin |

In addition, a compound of formula I or II shows useful effects in the treatment of disorders arising as a result of transplantation, for example, allogenic transplantation, especially tissue rejection, such as especially obliterative bronchiolitis (OB), i.e. a chronic rejection of allogenic lung transplants. In contrast to patients without OB, those with OB often show an elevated PDGF concentration in bronchoalveolar lavage fluids. If a compound of formula I or II is administered to rats with tracheal allogenic transplants, for example in a dose of 50 mg/kg i.p., it can be shown after removal of 10 transplants per group after 10 and 30 days for morphometric analysis of possible epithelial lesions and occlusion of the airways, and investigation for immunohistochemical pathways of action that, although a compound of formula I or II has no significant effect on epithelial necrosis or infiltration by inflammatory cells, it does markedly reduce fibroproliferation and occlusion of the lumen compared with controls. Synergistic effects with other immunomodulatory or anti-inflammatory substances are possible, for example when used in combination with cyclosporin A (CsA), rapamycin, or ascomycin, or immunosuppressant analogues thereof, for example cyclosporin G, FK-506 or comparable compounds; corticosteroids; cyclophosphamide; azathioprine; methotrexate; brequinar; leflunomide; mizoribine; mycophenolic acid; mycophenolate mofetil; 15-deoxyspergualin; immunsuppressant antibodies, especially monoclonal antibodies for leucocyte receptors, for example MHC, CD2, CD3, CD4, CD7, CD25, CD28, B7, CD45, CD58 or their ligands; or other immunomodulatory compounds, such as CTLA41g. If CsA (1 mg/kg s.c.), for example, is combined with a compound of formula I or II (50 mg/kg), synergism may be observed.

A compound of formula I or II is also effective in diseases associated with vascular smooth-muscle cell migration and proliferation (where PDGF and PDGF receptor often also play a role), such as restenosis and atherosclerosis. These effects and the consequences thereof for the proliferation or migration of vascular smooth-muscle cells in vitro and in vivo can be demonstrated by administration of a compound of formula I or II and also by investigating its effect on the thickening of the vascular intima following mechanical injury in vivo.

A compound of formula I or II is used in 0.1 N HCl or DMSO at a concentration of 10 mM for in vitro studies. The stock solution is further diluted with cell culture medium and used In concentrations of 10 to 0.1 µM for the experiments. For in vivo administration, a compound of formula I or II is dissolved for example in DMSO at a concentration of 200 mg/ml and then diluted 1:20 with 1% Tween in 0.9% saline solution. After sonication, a clear solution is obtained. The stock solutions are prepared fresh each day before administration. (The compound of formula I or II may also be dissolved simply in deionised water for oral administration or in 0.9% saline solution for parenteral administration). Administration is carried out 24 hours before the operation. A compound of formula I or II is administered to rats in one dose of 50 mg/kg i.p. per day for the entire observation period. Control rats are given the same formulation but without the presence of a compound of formula I or II. Oral administration is also possible.

Primary cultures of smooth-muscle aorta cells are isolated from 9 to 11-day-old DA (AG-B4, RT1a) rat aorta using a modification of the method described by Thyberg et al. (see Differentiation 25, 156-67 (1983)). The aorta is opened by means of a longitudinal incision and the endothelium carefully removed. The adventitia and the tunica media are separated, and the tunica media is digested with 0.1% collagenase and DNAse in phosphate-buffered physiological saline for 30 min at 37° C. The cells are centrifuged, suspended in culture medium, and then allowed to grow on plastic vials. The primary cells are used for the experiments after passages 2 to 6. Subcultures are kept in DMEM (Dulbecco's Modified Eagle's Medium), supplemented with 10% fetal calf serum, 2 mmol/ml glutamine, 100 mmol/ml streptomycin, and 100 IU/ml penicillin. For identification purposes, the cells are left to grow on glass slide covers and stained immunohistochemically using an anti-α-actin antibody obtained from smooth-muscle cells (see below).

The migration of smooth-muscle cells is quantified in vitro using a Transwell cell culture insert (Costar, Cambridge, Mass.) whose upper and lower compartments are separated by a polycarbonate membrane of 8 μm pore size. The cells (100 μl at a concentration of 1 million cells/ml) are exposed in the upper compartment. After 2 hours, 60 ng/ml PDGF-BB or PDGF-M (Upstate Biotechnology Inc., Lake Placid, N.Y.) is added to the lower compartment, supplemented with 0.5% fetal calf serum and 0.1% bovine serum albumin, and the test compound of formula I or II is added in concentrations of 3, 1, 0.3, 0.1, 0.03, 0.01, and 0.003 μM. To measure fibronectin-dependent migration, the Transwell chambers are covered with fibronectin at a concentration of 10 μg/ml for 24 h at 4° C. (human cellular fibronectin, Upstate Biotechnology Inc.). After 24 hours' migration, the filters are removed, fixed in methanol, and stained with Mayer's haematoxylin and eosin. The migrated cells on the lower side of the filter membrane are determined by counting the specified sectional fields on the filters with the aid of a light microscope with a magnification of 400×. The inhibition of migration is quantified in terms of the percentage of cells versus with the control. To exclude the possibility of a toxic effect, the viability of the cells is tested by incorporation of 3H-thymidine in DMEM, supplemented with 10% fetal calf serum. An inhibition of migration induced by PDGF-AA and especially by PDGF-BB is observed with a compound of formula I or II.

Experimental animals: the aorta and carotid artery of male Wistar rats (purchased from the Laboratory Animal Centre of the University of Helsinki, Finland) are denuded. The rats are anaesthetised with 240 mg/kg chloral hydrate i.p. and Buprenorphine (Temgesic, Reckitt & Coleman, Hull, UK) is administered for perioperative and postoperative alleviation of pain. All animals are given human care in keeping with the "Principles of Laboratory Animal Care" and the "Guide for the Care and Use of Laboratory Animals" of the NIH (NIH Publication 86-23, revised 1985). Rats weighing 200-300 g were used for the denudation procedure. The left common carotid artery is denuded of endothelium through the intraluminal passage of a 2F embolectomy catheter (Baxter Healthcare Corporation, Santa Ana, Calif., 27). To remove the endothelium, the catheter is passed through the lumen three times, inflated with 0.2 ml air. The external carotid is ligated after removal of the catheter and the wound closed. The histological changes are evaluated by reference to sections of mid-carotid 4 days after denudation. The thoracic aorta is denuded of endothelium using a 2F Fogarty arterial embolectomy catheter. The catheter is inserted into the thoracic aorta via the left iliac artery, inflated with 0.2 ml air, and passed through the lumen five times to remove the endothelium. The iliac artery is then ligated. Three times (3, 7 and 14 days) are selected for evaluation of the histological changes.

To quantify the proliferating cells, 3 different procedures are used for labelling the cells with bromodeoxyuridine (BrdU) after denudation of the rat carotid. In this model, the media cell proliferation begins 24 h after denudation; cells in the intima first appear after 72-96 hours. To quantify the proliferation of smooth-muscle cells before the appearance of cells in the intima, 0.1 ml BrdU-labelling reagent (ZYMED, San Francisco, Calif.) is administered i.v. during the postoperative period of 0 to 72 h post-denudation (in total 0.1 ml 6 times). To quantify the proliferation during the initial wave of migration, the rats were given 3×0.1 ml BrdU-labelling reagent at 8-hour intervals over a period of 72-96 hours after the operation. To quantify the proliferation at the end of the initial wave of migration, a third group of rats is given a pulsed dose of 0.3 ml BrdU three hours before sacrifice.

Histological samples are fixed in 3% paraformaldehyde solution for 4 h for embedding in paraffin. Morphological changes are evaluated from paraffin sections stained with Mayer's haematoxylin-eosin. The cell counts of different vessel sections are calculated at a magnification of 400×. To identify cells in culture and cells appearing in the neo-intima within four days of the denudation injury, immunohistochemical staining of acetone-fixed samples is carried out using an anti-a-actin antibody obtained from smooth-muscle cells (Bio-Makor, Rehovot, Israel). Primary smooth-muscle cells are identified on acetone-fixed glass cover slides using the same staining method. The sections are incubated with the primary antibody (dilution 1:2000), washed, and incubated consecutively with peroxidase-conjugated rabbit-antimouse-Ig and goat-antirabbit-Ig, followed by treatment with substrate solution with the chromogen 3-amino-9-ethylcarbazol and hydrogen peroxide. BrdU stains are prepared from paraffin sections using a primary mouse antibody (Bu20a, Dako, A/S, Denmark) and the Vectastain Elite ABC-Kit (Vector Laboratories, Burliname, Calif.). The sections are deparaffinised and treated by microwave at 500 W (2×5 min in 0.1 M citrate buffer, pH 6), followed by treatment with 95% formamide in 0.15 M trisodium citrate for 45 min at 70° C. Antibody dilutions are prepared according to the manufacturer's specifications. The sections are counterstained with Mayer's haematoxylin and eosin, and positive cells are counted separately for the intima, media, and adventitia.

In the carotid of treated animals, a significant decrease is found in the cell count for smooth-muscle cells. The adventitia and the media showed a significant reduction in the cell count. As a result of a compound of formula I or II, a slight decrease in the absolute number of BrdU-labelled cells is seen in the intima, media, and adventitia during the first two labelling periods (0-72 and 72-96 h), and after 93-96 h a decrease in the number of labelled cells is seen in all compartments. Decreases in the number of smooth-muscle cells are likewise found in the aorta-denuded animals.

According to these findings, a compound of formula I or II can thus inhibit the proliferation, and especially the migration, of vascular smooth-muscle cells.

A compound of formula I or II is also capable of inhibiting angiogenesis. This may be demonstrated as follows: a chamber containing agar (0.8%) and heparin (2 U/ml) with or without growth factor (VEGF 3 μg/ml, PDGF 1 μg/ml or bFGF 0.3 μg/ml) is implanted subcutaneously into normal mice (C57 BL/6). A compound of formula I or II is administered orally in a dose showing good anti-tumour activity in a nude mouse xenotransplant model. Dosing is started one day before implantation of the chambers. The chambers are removed after 5 days. The angiogenic efficacy is quantified by measuring both the vascularised tissue which has grown around the implant and the blood content of this tissue (external blood). The blood is determined by measuring the haemoglobin. Although the vessels do not grow into the agar, the agar becomes intensely red if an antiangiogenic effect is present. If a compound inhibits the increase in blood that is induced by the growth factor, this is seen as an indication that the compound in question is blocking the angiogenic effect of the growth factor concerned. Inhibition of the weight but not the volume of blood suggests an effect on the proliferation of fibroblasts. A suppression of the control response suggests an inhibition of wound healing. At an oral dose of 50 mg/kg once daily, a compound of formula I or II inhibits the angiogenic effect of all three growth factors (VEGF, PDFG, bFGF).

Interestingly, it was found that 4-[(4-methyl-1-piperazinyl)-methyl]-N-{4-hydroxymethyl-3-[[4-(3-pyridinyl)-2-pyrimidinyl]-amino]-phenyl}-benzamide, 4-[(4-methyl-4-oxido-1-piperazinyl)-methyl]-N-{4-methyl-3-[[4-(3-pyridinyl)-2-pyrimidinyl]-amino]-phenyl}-benzamide and 4-[(4-methyl-1-piperazinyl)-methyl]-N-[4-methyl-3-[[4-(1-oxido-3-pyridinyl)-2-pyrimidinyl]-amino]-phenyl]-benzamide represent metabolites of N-[4-methyl-3-(4-pyridin-3-yl-pyrimidin-2-ylamino)-phenyl]-4-(4-methyl-piperazin-1-ylmethyl)-benzamide (STI571 or imatinib, hereinafter compound A) which can be found in the human body upon administration of compound A. Compound A is described in EP 0 564 409 B1 and, in the form of the methane sulfonate salt, in WO 99/03854.

In addition to the before-mentioned metabolites, further compound A metabolites were identified in monkeys such as 4-[(4-methylcarbonyl-1-piperazinyl)-methyl]-N-{4-methyl-3-[[4-(3-pyridinyl)-2-pyrimidinyl]-amino]-phenyl}-benzamide, 4-[(4-methyl-1-piperazinyl)-methyl]-N-{4-carboxy-3-[[4-(3-pyridinyl)-2-pyrimidinyl]-amino]-phenyl}-benzamide, 4-carboxy-N-{4-methyl-3-[[4-(3-pyridinyl)-2-pyrimidinyl]-amino]-phenyl}-benzamide, 4-[(4-methyl-1piperazinyl)-methyl]-N-[4-methyl-3-[[4-(3-pyridinyl)-2-pyrimidinyl]-amino]-phenyl]-benzamide wherein the pyridinyl moiety is substituted at a ring carbon atom by hydroxy, and 4-[(1-piperazinyl)-methyl]-N-[4-methyl-3-[[4-(3-pyridinyl)-2-pyrimidinyl]-amino]-phenyl]-benzamide wherein the pyridinyl moiety is substituted at a ring carbon atom by hydroxy.

Preference is given to compounds of formula II, wherein $R_1$ is hydrogen, $R_2$ is methyl or hydroxymethyl, $R_3$ is methyl, and the stars indicate the nitrogen atoms which optionally carry an oxygen atom to form the corresponding N-oxides, with the proviso that at least one of the three nitrogen atoms marked by a star carries an oxygen atom if $R_2$ is methyl, or salts of such compounds.

Special preference is further given to compounds of formula II, wherein $R_1$ is hydrogen, $R_2$ is hydroxy-lower alkyl, $R_3$ is methyl, and the stars indicate the nitrogen atoms which optionally carry an oxygen atom to form the corresponding N-oxides, or salts of such compounds.

Especially preferred are the compounds selected from 4-[(4-methyl-1-piperazinyl)-methyl]-N-{4-hydroxymethyl-3-[[4-(3-pyridinyl)-2-pyrimidinyl]-amino]-phenyl}-benzamide, 4-[(4-methyl-4-oxido-1-piperazinyl)-methyl]-N-{4-methyl-3-[[4-(3-pyridinyl)-2-pyrimidinyl]-amino]-phenyl}-benzamide and 4-[(4-methyl-1-piperazinyl)-methyl]-N-[4-methyl-3-[[4-(1-oxido-3-pyridinyl)-2-pyrimidinyl]-amino]-phenyl]-benzamide, and pharmaceutically acceptable salts of these compounds.

Very special preference is further given to a compound of formula I or II mentioned In the Examples below, or a salt, especially a pharmaceutically acceptable salt, thereof.

The compounds of formula I or II or salts thereof are prepared in accordance with processes known per se, though not previously described for the manufacture of the compounds of the formula I or II, especially whereby a) a compound of formula III

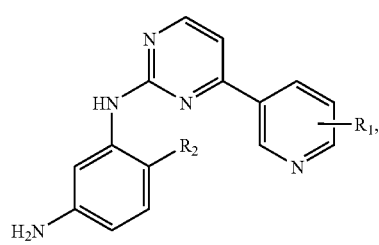

(III)

wherein $R_1$ and $R_2$ have the meanings given under formula I, is reacted with a compound of formula IV

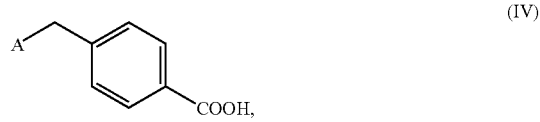

(IV)

wherein A has the meanings given under formula I.

and a compound thus obtained is converted into a N-oxide of formula I with a suitable oxidizing agent or if not converted into a N-oxide, A has to be substituted by oxo on a ring carbon;

preferably, a compound of formula III

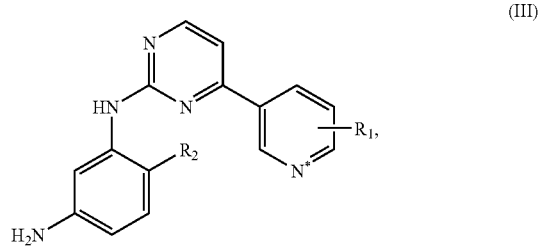

(III)

wherein $R_1$ and $R_2$ have the meanings given under formula II and the star indicates a nitrogen atom which optionally carries an oxygen atom, is reacted with a compound of formula IV

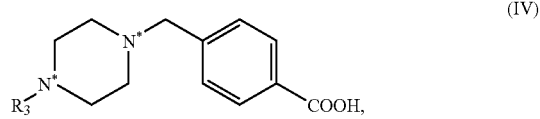

(IV)

wherein $R_3$ has the meanings given under formula II and the stars indicate the nitrogen atoms which optionally carry an oxygen atom;

and a compound thus obtained is optionally converted into a N-oxide of formula II with a suitable oxidizing agent; or b) a compound of formula V

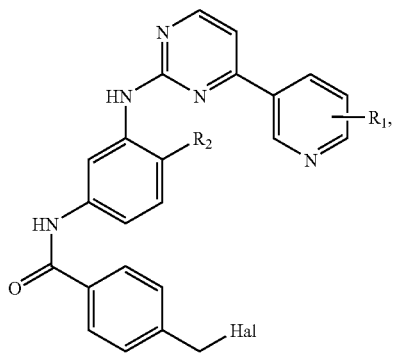

(V)

wherein $R_1$ and $R_2$ have the meanings given under formula I, Hal is halo (e.g. —Cl, —Br, —F, —I), is reacted with a compound of formula VI

AH  (VI), wherein A has the meanings given under formula I, and a compound thus obtained is optionally converted into a N-oxide of formula I with a suitable oxidizing agent;

preferably, a compound of formula V

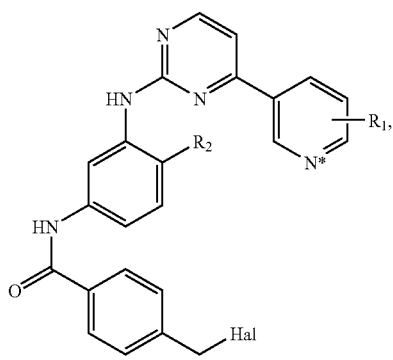

(V)

wherein $R_1$ and $R_2$ have the meanings given under formula II, Hal is halo (e.g. —Cl, —Br, —F, —I) and the star indicates a nitrogen atom which optionally carries an oxygen atom, is reacted with a compound of formula VI

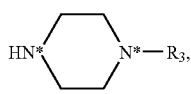

(VI)

wherein $R_3$ has the meanings given under formula II and the stars indicate the nitrogen atoms which optionally carry an oxygen atom;

and a compound thus obtained is optionally converted into a N-oxide of formula II with a suitable oxidizing agent;

whereby functional groups which are present in the starting compounds of process a) or b) and are not intended to take part in the reaction, are present in protected form if necessary, and protecting groups that are present are cleaved, whereby the said starting compounds may also exist in the form of salts provided that a salt-forming group is present and a reaction in salt form is possible;

and, if so desired, a compound of formula I or II obtained by process a) or b) is converted into another compound of formula I or II, an obtained free compound of formula I or II is converted into a salt, an obtained salt of a compound of formula I or II is converted into the free compound or another salt, and/or a mixture of isomeric compounds of formula I or II is separated into the individual isomers.

In a most preferred embodiment, compounds of formula I or II are in a substantially pure form.

The term "substantially pure" is understood in the context of the present invention to mean substantially free of biological material such as found in the blood, especially less than 10%, preferably less than 1%, and most preferably free of such biological material.

DESCRIPTION OF THE PROCESS VARIANTS

A suitable oxidizing agent for converting a compound obtained by process a) or b) into a N-oxide of formula I or II is preferably hydrogen peroxide or a suitable peracid, for example a suitable perbenzoic acid, such as especially m-chloro-perbenzoic acid. The reaction is carried out in an inert solvent, for example a halogenated hydrocarbon, such as dichloromethane, at temperatures of approximately from −20° C. to the boiling point of the solvent in question, in general below +100° C. If hydrogen peroxide is used as the oxidizing agent, the reaction is preferably carried out in water at about room temperature. The desired N-oxide can then be purified using conventional methods such as e.g. column chromatography or recrystallisation.

On the other hand, the N-oxides of formula I or II may be prepared according to the process described in the preceding paragraph by already oxidizing the starting materials used in the synthesis of compounds of formula I or II.

Regarding Process a):

The reaction between a compound of formula III and a compound of formula IV preferably takes place in a suitable inert solvent, especially N,N-dimethylformamide, in the presence of propylphosphonic anhydride (Fluka, Buchs, Switzerland) and a base such as especially triethylamine, preferably at room temperature.

Regarding Process b):

The reaction between a compound of formula V and a compound of formula IV preferably takes place in a suitable inert solvent, especially alcohols, e.g. lower alcohols such as especially ethanol, at elevated temperature, preferably near the boiling temperature of the solvent employed.

Halo present in a compound of formula V is e.g. fluoro, chloro, bromo and iodo, preferably chloro.

Additional Process Steps

In the additional process steps, carried out as desired, functional groups of the starting compounds which should not take part in the reaction may be present in unprotected form or may be protected for example by one or more protecting groups. The protecting groups are then wholly or partly removed according to one of the known methods.

Protecting groups, and the manner in which they are introduced and removed are described, for example, in "Protective Groups in Organic Chemistry", Plenum Press, London, New York 1973, and in "Methoden der organischen Chemie", Houben-Weyl, 4th edition, Vol. 15/1, Georg-Thieme-Verlag, Stuttgart 1974 and in Theodora W. Greene, "Protective Groups in Organic Synthesis", John Wiley & Sons, New York 1981. A characteristic of protecting groups is that they can be removed readily, i.e. without the occurrence of undesired secondary reactions, for example by solvolysis, reduction, photolysis or alternatively under physiological conditions.

The end products of formula I or II may however also contain substituents that can also be used as protecting groups in starting materials for the preparation of other end products of formula I or II. Thus, within the scope of this text, only a readily removable group that is not a constituent of the particular desired end product of formula I is designated a "protecting group", unless the context indicates otherwise.

GENERAL PROCESS CONDITIONS

All process steps described here can be carried out under known reaction conditions, preferably under those specifically mentioned, in the absence of or usually in the presence of solvents or diluents, preferably those that are inert to the reagents used and able to dissolve them, in the absence or presence of catalysts, condensing agents or neutralising agents, for example ion exchangers, typically cation exchangers, for example in the protonated ($H^+$-) form, depending on the type of reaction and/or reactants at reduced, normal, or elevated temperature, for example in the range from $-100°$ C. to about $190°$ C., preferably from about $-80°$ C. to about $150°$ C., for example at $-80$ to $-60°$ C., at RT, at $-20$ to $40°$ C., at 0 to $100°$ C. or at the boiling point of the solvent used, under atmospheric pressure or in a closed vessel, if need be under pressure, and/or in an inert, for example an argon or nitrogen, atmosphere.

The invention relates also to those embodiments of the process in which one starts from a compound obtainable at any stage as an intermediate and carries out the missing steps, or breaks off the process at any stage, or forms a starting material under the reaction conditions, or uses said starting material in the form of a reactive derivative or salt, or produces a compound obtainable by means of the process according to the invention under those process conditions, and further processes the said compound in situ. In the preferred embodiment, one starts from those starting materials which lead to the compounds described hereinabove as preferred.

In the preferred embodiment, a compound of formula I or II is prepared according to the processes and process steps defined in the Examples.

The compounds of formula I or II, including their salts, are also obtainable in the form of hydrates, or their crystals can include for example the solvent used for crystallisation (present as solvates).

Starting Materials

New starting materials and/or intermediates, as well as processes for the preparation thereof, are likewise the subject of this invention. In the preferred embodiment, such starting materials are used and reaction conditions so selected as to enable the preferred compounds to be obtained.

The starting materials used in the above described process are known, capable of being prepared according to known processes (see also EP 0 564 409 B1), or commercially obtainable; in particular, they can be prepared using processes as described in the Examples.

In the preparation of starting materials, existing functional groups which do not participate in the reaction should, if necessary, be protected. Preferred protecting groups, their introduction and their removal are described above or in the Examples. In place of the respective starting materials and transients, salts thereof may also be used for the reaction, provided that salt-forming groups are present and the reaction with a salt is also possible. Where the term starting materials is used hereinbefore and hereinafter, the salts thereof are always included, insofar as reasonable and possible.

A compound of formula III wherein $R_2$ is lower alkyl and the nitrogen atom marked by a star does not carry an oxygen atom as a substituent can be prepared as described in EP 0 564 409 B1. Such compounds may then be converted into the corresponding N-oxides using a suitable oxidizing agent as described above under "Description of the process variants".

A compound of formula III wherein $R_2$ is hydroxy-lower alkyl can be prepared analogously to Example 1 by starting with a compound of the following formula VII:

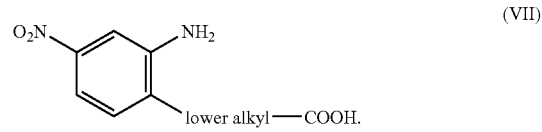

The remaining starting materials are known, capable of being prepared according to known processes like those described in e.g. EP 0 564 409 B1, or commercially available; or in particular, they can be prepared using processes as described in the Examples. Suitable N-phenyl-2-pyrimidine-amine derivatives to form the corresponding N-oxides are also described in e.g. EP 0 564 409 B1.

The invention relates also to a process for the treatment of warm-blooded animals, including humans, suffering from said diseases, especially a tumour disease, wherein a quantity of a compound of formula I or II which is effective against the disease concerned, especially a quantity with antiproliferative and especially tumour-inhibiting efficacy, is administered to warm-blooded animals, Including humans, in need of such treatment. The invention relates moreover to the use of a compound of formula I or II for the inhibition of the above-mentioned tyrosine kinases, especially PDGF receptor kinase, v-Abl kinase, and/or c-Kit receptor kinase, or for the preparation of pharmaceutical compositions for use in treating warm-blooded animals, including humans, especially for the treatment of tumours, such as gliomas, ovarian tumours, prostate tumours, colon tumours, and tumours of the lung, such as especially small cell lung carcinoma, and tumours of the breast or other gynaecological tumours. Depending on species, age, individual condition, mode of administration, and the clinical picture in question, effective doses, for example daily doses of about 1-2500 mg, preferably 1-1000 mg, especially 5-500 mg, are administered to warm-blooded animals, including humans, of about 70 kg bodyweight.

Thus, in a further aspect, the present invention relates to the use of N-phenyl-2-pyrimidine—amine derivatives in which at least one nitrogen atom carries an oxygen atom to form the corresponding N-oxides or a pharmaceutically acceptable salt of such a compound for the preparation of a pharmaceutical composition for the treatment of a proliferative disorder.

Preferably, the present invention relates to the use of a compound of formula I or II or a pharmaceutically acceptable salt of such a compound for the preparation of a pharmaceutical composition for the treatment of a proliferative disorder.

Most preferably, the proliferative disorder is selected from tumors or brain proliferative disorders.

The invention further provides a method of treating warm-blooded animals, including humans, which comprises administering to such a warm-blooded animal suffering from a proliferative disorder, in a dose effective against said disorder, a compound of formula I or II or a pharmaceutically acceptable salt of such a compound.

In still another embodiment, the instant invention provides a pharmaceutical composition comprising at least one N-phenyl-2-pyrimidine-amine derivative in which at least one nitrogen atom carries an oxygen atom to form the corresponding N-oxides or a pharmaceutically acceptable salt thereof, together with a pharmaceutically acceptable carrier.

Preferably, the instant invention provides a pharmaceutical composition comprising a compound of formula I or II or a pharmaceutically acceptable salt thereof, together with a pharmaceutically acceptable carrier.

The compositions of the present invention may contain at least one additional pharmaceutically active compound such as 4-(4-methylpiperazin-1-ylmethyl)-N-[4-methyl-3-(4-pyridin-3-yl)pyrimidin-2-ylamino)phenyl]-benzamide.

Preferably a pharmaceutical composition for the treatment of a proliferative disorder in warm-blooded animals, including humans, comprising as an active ingredient a compound of formula I or II according or a pharmaceutically acceptable salt of such a compound, together with a pharmaceutically acceptable carrier.

Thus the invention relates also to pharmaceutical compositions comprising as an active ingredient a compound of formula I or II together with a pharmaceutically acceptable carrier, especially for the prevention or treatment of one of the said diseases, said pharmaceutical compositions being suitable for e.g. topical, enteral, for example oral or rectal, or parenteral administration. Especially tablets or gelatin capsules containing the active substance together with diluents, for example lactose, dextrose, sucrose, mannitol, sorbitol, cellulose, and/or glycerin, and/or lubricants, for example silica, talc, stearic acid, or salts thereof, typically magnesium or calcium stearate, and/or polyethylene glycol, are used for oral administration. Tablets may likewise contain binders, for example magnesium aluminium silicate, starches, typically corn, wheat or rice starch, gelatin, methylcellulose, sodium carboxymethylcellulose and/or polyvinylpyrrolidone, and, if so desired, disintegrants, for example starches, agar, alginic acid, or a salt thereof, typically sodium alginate, and/or effervescent mixtures, or adsorbents, colouring agents, flavours, and sweetening agents. The pharmacologically active compounds of the present invention may further be used in the form of preparations for parenteral administration or infusion solutions. Such solutions are preferably isotonic aqueous solutions or suspensions, these possibly being prepared before use, for example in the case of lyophilised preparations containing the active substance either alone or together with a carrier, for example mannitol. The pharmaceutical substances may be sterilised and/or may contain excipients, for example preservatives, stabilisers, wetting agents and/or emulsifiers, solubilisers, salts for the regulation of osmotic pressure, and/or buffers. The present pharmaceutical compositions which, if so desired, may contain further pharmacologically active substances, such as other c-Kit inhibitors or inhibitors of VEGF receptor or c-Src activity, are prepared in a manner known per se, for example by means of conventional mixing, granulating, coating, dissolving or lyophilising processes, and contain from about 1% to 100%, especially from about 1% to about 20%, of the active substance or substances.

EXAMPLES

The following Examples illustrate the invention but do not limit the scope thereof in any way.

| Abbreviations: | |
| --- | --- |
| DMF | N,N-Dimethylformamide |
| h | hour(s) |
| min | minute(s) |
| m.p. | melting point |
| RT | room temperature |
| THF | tetrahydrofuran |

Example 1

4-[(4-Methyl-1-piperazinvi)-methyl]-N-{4-hydroxymethyl-3-[[4-(3-pyridinyl)-2-Pnrimidinyl]-amino]-phenyl}-benzamide A solution of propylphosphonic anhydride in N,N-dimethylformamide (Fluka, Buchs, Switzerland; 350 µL of 50%, 0.6 mmol) is added in portions over 20 min to a stirred mixture of N-(5-amino-2-hydroxymethyl-phenyl)-4-(3-pyridinyl)-2-pyrimidinamine (117 mg, 0.4 mmol), 4-[(4-methyl-1-piperazinyl)-methyl]-benzoic acid dihydrochloride (123 mg, 0.4 mmol) and triethylamine (445 µL, 3.2 mmol) in dry N,N-dimethylformamide (5 mL). The mixture is stirred for 24 h at RT. The solvent is evaporated off under reduced pressure and the residue is treated with saturated aqueous sodium hydrogen carbonate solution (20 mL) and extracted with ethyl acetate (2×20 mL). The combined extracts are washed with saturated aqueous sodium chloride (15 mL), dried (MgSO$_4$), filtered and the solvent is evaporated off under reduced pressure to yield the crude product which is purified by reverse phase high pressure liquid chromatography (Nagel Polygoprep C$_{18}$, 7 µm, 300 Å; Macherey-Nagel, Duren, Germany), eluent 0.1% trifluoroacetic acid in water −0.1% trifluoroacetic acid in acetonitrile. The fractions containing the pure product are combined, basified with saturated aqueous sodium hydrogen carbonate and evaporated to dryness under reduced pressure. The residue is treated with saturated aqueous sodium hydrogen carbonate and extracted with ethyl acetate (5×). The combined extracts are washed with water, dried (MgSO$_4$), filtered and the solvent is evaporated off under reduced pressure to yield the product which is recrystallised from methanol—ethyl acetate to give the title compound as a pale-yellow crystalline solid, m.p. 196-198° C.

$^1$H-NMR (500 MHz, DMSO-d$_6$, δ): 2.14 (s, 3H), 2.25-2.45 (m, 8H), 3.52 (s, 2H), 4.56 (s, 2H), 5.50 (br.s, 1H), 7.29 (d, J=8.3 Hz, 1H), 7.41 (dd, J=2.0, 8.3 Hz, 1H), 7.44 (d, J=8.1 Hz, 2H), 7.50 (d, J=5.1 Hz, 1H), 7.52 (dd, J=3.3, 8.1 Hz, 1H), 7.93 (d, J=8.1 Hz, 2H), 8.56 (d, J=2.0 Hz, 1H), 8.57 (d, J=5.1 Hz, 1H), 8.59 (ddd, J=1.4, 2.1, 8.1 Hz, 1H), 8.69 (dd, J=1.4, 3.3 Hz, 1H), 9.10 (s, 1H), 9.33 (d, J=2.1 Hz, 1H) and 10.22 (s, 1H).

Step 1.1: 2-Amino-4-nitrobenzenemethanol

A stirred solution of 2-amino-4-nitrobenzoic acid (Aldrich; 18.2 g, 100 mmol) in dry THF (500 mL) at 20° C., is treated with a solution of borane-THF complex (BH$_3$-THF; Fluka; 100 mL of 1.0 M), dropwise over 45 min to regulate the gas evolution. The mixture is then heated at 65° C. for 2 h. The stirred mixture is then cooled to 0° C., treated with water (20 mL) and warmed to RT. Upon the cessation of gas evolution, hydrochloric acid (20 mL of 12 M) is added and the mixture is then heated at 65° C. for 30 min. The cooled mixture is then concentrated to a volume of circa 150 mL by rotary evaporation under reduced pressure to give a suspension. The suspension is filtered and the precipitate is redissolved in ethyl acetate (500 mL) and washed with saturated aqueous sodium hydrogen carbonate (2×150 mL). The solution is dried ($Na_2SO_4$), filtered and the solvent is evaporated off under reduced pressure to yield the crude product which is purified by recrystallisation from ethyl acetate-hexane to give the title compound as a yellow crystalline solid, m.p. 126-128° C.

Step 1.2: 2-[(2-Propenyloxy)-methyl]-5-nitrobenzenamine

A stirred solution of 2-amino-4-nitrobenzenemethanol (14.3 g, 85 mmol) in dry THF (350 mL) at 0° C. under an argon atmosphere, is treated dropwise over 35 min with a solution of potassium tert-butylate in THF (Fluka; 85 mL of 1.0 M). The mixture is stirred at 0° C. for 15 min and then treated dropwise over 50 min with a solution of allylbromide (7.9 mL, 94 mmol) in dry THF (80 mL) at 0° C. and then stirred at 20° C. for 90 min. The mixture is diluted with ethyl acetate (800 mL). The resulting solution is washed with saturated aqueous ammonium chloride (3×400 mL), dried ($MgSO_4$), filtered and the solvent is evaporated off under reduced pressure to yield the crude product which is purified by column chromatography on silica gel, eluent 50% ethyl acetate in hexane, to give the title compound as a brown oil.

$^1$H-NMR (500 MHz, DMSO-$d_8$, δ): 4.06 (d, J=5.3 Hz, 2H); 4.47 (s, 2H); 5.22 and 5.34 (dd, J=10.4, 17.3 Hz, 2H); 5.65 (br.s, 2H); 5.98 (m, J=5.3, 10.4, 17.3 Hz, 1H), 7.35 (d, J=8.3 Hz, 1H), 7.38 (dd, J=2.0, 8.3 Hz, 1H) and 7.52 (d, J=2.0 Hz, 1H).

Step 1.3: {2-[(2-Propenyloxy)-methyl]-5-nitrophenyl}-guanidine

Nitric acid (1.04 mL of 65%, 15 mmol) is added to a stirred solution of 2-[(2-propenyloxy)-methyl]-5-nitrobenzenamine (3.15 g, 15 mmol) in ethanol (30 mL) at 200C. A solution of cyanamide (0.95 g, 22.5 mmol) in water (1 mL) is then added dropwise to the stirred mixture at 95° C. over a period of 60 min. The mixture is heated at 95° C. for 14 h, with additional aliquots of cyanamide (total 2.2 g, 58 mmol) being added throughout this period and with the acidity being periodically adjusted to pH 3 by the addition of nitric acid (65%). The resulting mixture is cooled to 0° C., basified with aqueous ammonia (5 mL of 25%), diluted with water (150 mL) and extracted with ethyl acetate (3×100 mL). The combined extracts are washed with saturated aqueous ammonium chloride (50 mL), dried ($MgSO_4$), filtered and the solvent is evaporated off under reduced pressure to give the title compound as a brown oil, which is used directly in the next step without further purification.

Step 1.4: N-{2-[(2-Propenyloxy)-methyl]-5-nitro-phenyl}-4-(3-pyridinyl)-2-pyrimidinamine A stirred mixture of {2-[(2-propenyloxy)-methyl]-5-nitrophenyl}-guanidine (3.75 g, 15 mmol), 3-(dimethylamino)-1-(3-pyridinyl)-2-propen-1-one (2.60 g, 15 mmol) and ethyl diisopropylamine (2.6 mL, 15 mmol) in 1-butanol (50 mL) is heated at 120° C. for 20 h. The solvent is then evaporated off under reduced pressure to give a residue which is dissolved in ethyl acetate (100 mL). The resulting mixture is filtered (celite), washed with saturated aqueous sodium chloride (50 mL), dried ($MgSO_4$), filtered and the solvent is evaporated off under reduced pressure to yield the crude product which is purified by column chromatography on silica gel, eluent ethyl acetate, and recrystallised from ethyl acetate-hexane to give the title compound as a yellow crystalline solid, m.p. 213-2150C.

$^1$H-NMR (500 MHz, DMSO-$d_6$, δ): 4.10 (d, J=5.3 Hz, 2H); 4.77 (s, 2H); 5.22 and 5.35 (dd, J=10.4, 17.3 Hz, 2H); 5.96 (m, J=5.3,10.4, 17.3 Hz, 1H), 7.58 (dd, J=4.8, 7.9 Hz, 1H), 7.66 (d, J=8.4 Hz, 1H), 7.69 (d, J=5.2 Hz, 1H), 7.95 (ddd, J=1.2, 1.2, 7.9 Hz, 1H), 8.51 (dd, J=1.6, 8.4 Hz, 1H), 8.67 (d, J=5.2 Hz, 1H), 8.73 (dd, J=1.2, 4.8 Hz, 1H), 9.05 (d, J=1.2 Hz, 1H), 9.23 (br.s, 1H) and 9.35 (d, J=1.6 Hz, 1H).

Step 1.5: N-(2-Hydroxymethyl-5-nitro-phenyl)-4-(3-pyridinyl)-2-pyrimidinamine

Polymethylhydrosiloxane (860 mg), tetrakis(triphenylphoshine)palladium (70 mg) and zinc chloride (2.66 mL of 0.5 M in THF, 1.33 mmol) is added to a stirred solution of N-{2-[(2-propenyloxy)-methyl]-5-nitro-phenyl}-4-(3-pyridinyl)-2-pyrmidinamine (2.60 g, 7.2 mmol) in dry THF (60 mL). The mixture is then stirred under an argon atmosphere at 30° C. for 30 h. The solvent is then evaporated off under reduced pressure to give a residue which is treated with saturated aqueous sodium chloride solution (50 mL) and extracted with ethyl acetate (3×50 mL). The combined extracts are dried ($Na_2SO_4$), filtered and the solvent is evaporated off under reduced pressure to yield the crude product which is recrystallised from THF to give the title compound as a pale-yellow crystalline solid, m.p. 247-250° C.

Step 1.6: N-(5-Amino-2-hydroxymethyl-phenyl)-4-(3-pyridinyl)-2-pyrimidinamine

A solution of N-(2-hydroxymethyl-5-nitro-phenyl)-4-(3-pyridinyl)-2-pyrimidinamine (0.23 g, 0.71 mmol) in ethanol (230 mL) is hydrogenated at atmospheric pressure over Raney nickel (0.2 g) at 25° C.. The calculated amount of hydrogen is taken up in 13 h. The mixture is then filtered and the solvent is evaporated off under reduced pressure to yield the crude product which is purified by column chromatography on silica gel, eluent 25% aqueous ammonia-ethanol-dichloromethane (1:9:90), to give the title compound as a yellow crystalline solid, m.p. 213-215° C.

$^1$H-NMR (500 MHz, DMSO-$d_6$, δ): 4.42 (d, J=5.1 Hz, 2H), 5.05 (br.s, 2H), 5.26 (t, J=5.1 Hz, 1H), 6.23 (dd, J=2.1, 8.0 Hz, 1H), 6.91 (d, J=8.0 Hz, 1H), 7.35 (d, J=2.0 Hz, 1H), 7.45 (d, J=5.1 Hz, 1H), 7.56 (dd, J=4.7, 8.0 Hz, 1H), 8.47 (ddd, J=1.8, 1.8, 8.0 Hz, 1H), 8.53 (d, J=5.1 Hz, 1H), 8.70 (dd, J=1.4, 4.7 Hz, 1H), 8.88 (s, 1H) and 9.29 (d, J=2.4 Hz, 1H).

Example 2

4-[(4-Methyl-4-oxido-1-piperazinyl)-methyl]-N-[4-methyl-3-[[4-(3-pyridinyl)-2 Pyrimidinyl]-amino]-phenyl]-benzamide 3-Chloroperoxybenzoic acid (Fluka, Buchs, Switzerland; 2.06 g of 55%, 4.27 mmol) is added to a stirred mixture of 4-[(4-methyl-1-piperazinyl)-methyl]-N-{4-methyl-3-[[4-(3-pyridinyl)-2-pyrimidinyl]-amino]-phenyl}-benzamide (prepared as described in EP 0 564 409 B1, Example 21; 2.00 g, 4.05 mmol) in dichloromethane (70 mL) at −20° C. The resulting mixture is then stirred at RT for 72 h. The solvent is then evaporated off under reduced pressure to yield a mixture which is purified by column chromatography on silica gel, eluent dichloromethane-methanol-water (70:30:5), to give the title compound as a yellow crystalline solid, m.p. 154-158° C.

Example 3

4-[(4-Methyl-1-piperazinyl)-methyl]-N-[4-methyl-3-[[4-(1-oxido-3-pyridinyl)-2-pyrimidinyl]-amino]-phenyl]-benzamide N-Methylpiperazine (99 mg, 1.0 mmol) is added to a stirred suspension of 4-chloromethyl-N-[4-methyl-3-[[4-(1-oxido-3-pyridinyl)-2-pyrimidinyl]-amino]-phenyl]-benzamide (220 mg, 0.49 mmol) In ethanol (5 mL). The mixture is then stirred at 10° C. for 15 h to give a solution, which is then cooled to RT and treated with ethyl acetate (200 mL). The resulting solution is washed with aqueous sodium hydroxide (100 mL of 2M) and saturated aqueous sodium chloride solution (100 mL), dried ($Na_2SO_4$), filtered and the solvent is evaporated off under reduced pressure to yield the crude product which is purified by column chromatography on silica gel, eluent 25% aqueous ammonia-methanol-dichloromethane (0.5:10:90) to give the title compound as a yellow crystalline solid, m.p. 232-235° C.

Step 3.1: N-[4-Methyl-3-[[4-(1-oxido-3-pyridinyl)-2-pyrimidinyl]-amino]-phenyl]-benzamide Utilising the procedure described in Example 2, but employing N-[4-methyl-3-[[4-(3-pyridinyl)-2-pyrimidinyl]-amino]-phenyl]-benzamide (prepared as described in EP 0 564 409 B1, Example 20) in place of 4-[(4-methyl-1-piperazinyl)-methyl]-N-{4-methyl-3-[[4-(3-pyridinyl)-2-pyrimidinyl]-amino]-phenyl}-benzamide, afforded the title compound which is purified by column chromatography on silica gel, eluent 10% methanol in dichloromethane, and recrystallised from ethanol to give the title compound as a pale-yellow crystalline solid, m.p. 258-260° C.

Step 3.2: 4-Methyl-N-3-[4-(1-oxido-3-pyridinyl)-2-pyrimidinyl-1.3-benzenediamine Hydrochloric acid (9 mL of 4M) is added to a suspension of N[4-methyl-3-[[4-(1-oxido-3-pyridinyl)-2-pyrimidinyl]-amino]-phenyl]-benzamide (0.43 g, 1.08 mmol) in n-propanol (9 mL) and the resulting mixture is heated at 100° C. for 34 h. The cooled mixture is evaporated under reduced pressure to give an oil, which is dissolved in water (10 mL), filtered and basified with aqueous sodium hydroxide (4 M). The resulting precipitate is filtered, washed with water and dried to yield the crude product, which is recrystallised from ethanol to give the title compound as a yellow crystalline solid, m.p. 104-106° C.

Step 3.3: 4-Chloromethyl-N-[4-methyl-3-[[4-(1-oxido-3-pyridinyl)-2-pyrimidinyl]-amino]-phenyl]-benzamide A solution 4-(chloromethyl)-benzoyl chloride (Fluka, Buchs, Switzerland; 184 mg, 0.977 mmol) in dioxane (2 mL) is added dropwise to a solution of 4-methyl-N-3-[4-(1-oxido-3-pyridinyl)-2-pyrimidinyl]-1,3-benzenediamine (275 mg, 0.937 mmol) in dioxane (5 mL) and the mixture is stirred at 20° C. for 75 min. A second portion of 4-(chloromethyl)-benzoyl chloride (60 mg, 0.317 mmol) dissolved in dioxane (1 mL) is then added and the mixture is stirred for a further 120 min. The resulting suspension is treated with ethyl acetate (50 mL) to give a solution which is washed with aqueous sodium hydroxide (2×50 mL of 2M). The ethyl acetate solution is dried ($Na_2SO_4$), filtered and the solvent is evaporated off under reduced pressure to yield the crude product which is purified by column chromatography on silica gel, eluent 5% methanol in dichloromethane to give the title compound as a yellow crystalline solid, m.p. 224-226° C.

Example 4

4-[(4-Methyl-1.4-dioxido-1-piperazinyl)-methyl]-N-{4-methyl-3-[[4-(3-pyridinyl)-2-pyrimidinyl]-amino]-phenyl}-benzamide 4-[(4-Methyl-1-piperazinyl)-methyl]-N-{4-methyl-3-[[4-(3-pyridinyl)-2-pyrimidinyl]-amino]-phenyl}-benzamide monomethanesulphonate (3.00 g, 5 mmol; prepared as described in WO 99/03854) is added to aqueous hydrogen peroxide (30 mL of 3%) and the resulting solution is stirred at 20° C. for 160 h. The pH of the solution is then adjusted to pH 14 with aqueous sodium hydroxide (4 M) and the resulting suspension is stirred for 1.5 h. The crude product is filtered off, washed with water, dried and purified by column chromatography on silica gel, eluent 25% aqueous ammonia-ethanol-dichloromethane (5:30:70), to give the title compound as a yellow crystalline solid, m.p. 242-244° C.

Example 5

4-[(4-methyl-1-piperazinyl)methyl]-N-[4-hydroxymethyl-3-[[4-(3-pyridinyl)-2-pyrimidinyl]amino]phenyl]benzamide A solution of propylphosphonic anhydride in N,N-dimethylformamide (Fluka, Buchs, Switzerland; 350 µL of 50%, 0.6 mmol) is added in portions over 20 minutes to a stirred mixture of N-[2-[5-amino-(2-hydroxy)methyl]phenyl]-4-(3-pyridinyl)-2-pyrimidinamine as described in example 1, step 1.6 (117 mg, 0.4 mmol), 4-[(4-methyl-1-piperazinyl)methyl] benzoic acid, dihydrochloride (123 mg, 0.4 mmol) and triethylamine (445 µL, 3.2 mmol) in dry N,N-dimethylformamide (5 mL). The mixture is stirred for 24 hours at room temperature. The solvent is evaporated off under reduced pressure and the residue is treated with saturated aqueous sodium hydrogen carbonate solution (20 mL) and extracted with ethyl acetate (2×20 mL). The combined extracts are washed with saturated aqueous sodium chloride (15 mL), dried ($MgSO_4$), filtered and the solvent is evaporated off under reduced pressure to yield the crude product which is purified by reverse phase high pressure liquid chromatography (Nagel Polygoprep $C_{18}$, 7 µm, 300 Å; Macherey-Nagel, Düren, Germany), eluent 0.1% trifluoroacetic acid in water −0.1% trifluoroacetic acid in acetonitrile. The fractions containing the pure product are combined, basified with saturated aqueous sodium hydrogen carbonate and evaporated to dryness under reduced pressure. The residue is treated with saturated aqueous sodium hydrogen carbonate and extracted with ethyl acetate (5×). The combined extracts are washed with water, dried ($MgSO_4$), filtered and the solvent is evaporated off under reduced pressure to yield the product which is recrystallised from methanol—ethyl acetate to give the title compound as a pale-yellow crystalline solid, m.p. 196-198° C.

$^1$H-NMR (500 MHz, DMSO-$d_6$, δ):2.14 (s, 3H), 2.25-2.45 (m, 8H), 3.52 (s, 2H), 4.56 (s, 2H), 5.50 (br.s, 1H), 7.29 (d, J=8.3 Hz, 1H), 7.41 (dd, J=2.0, 8.3 Hz, 1H), 7.44 (d, J=8.1 Hz, 2H), 7.50 (d, J=5.1 Hz, 1H), 7.52 (dd, J=3.3, 8.1 Hz, 1H), 7.93 (d, J=8.1 Hz, 2H), 8.56 (d, J=2.0 Hz, 1H), 8.57 (d, J=5.1 Hz,

1H), 8.59 (ddd, J=1.4, 2.1, 8.1 Hz, 1H), 8.69 (dd, J=1.4, 3.3 Hz, 1H), 9.10 (s, 1H), 9.33 (d, J=2.1 Hz, 1H) and 10.22 (s, 1H).

Example 6

4-[(3-Oxo-1-piperazinyl)methyl]-N-[4-methyl-3-[[4-(3-pyridinyl)-2-pyrimidinyl]amino]phenyl]benzamide A solution of propylphosphonic anhydride in N,N-dimethylformamide (Fluka, Buchs, Switzerland; 1.3 mL of 50%, 2.25 mmol) is added dropwise to a stirred mixture of 4-methyl-N-[4-(3-pyridinyl)-2-pyrimidinyl]-1,3-benzenediamine (416 mg, 1.5 mmol), 4-[(3-oxo-1-piperazinyl)methyl]benzoic acid (351 mg, 1.5 mmol) and triethylamine (1.7 mL, 12 mmol) in dry N,N-dimethylformamide (4 mL). The mixture is stirred for 17 hours at room temperature and then treated with saturated aqueous sodium hydrogen carbonate solution (100 mL). The resulting precipitate is filtered, washed with water, dried and recrystallised from methanol to give the title compound as a cream crystalline solid.

$^1$H-NMR (500 MHz, DMSO-$d_6$, δ) ppm 2.21 (s, 3H), 2.63 (t, J=5.49 Hz, 2H), 2.80 (s, 3H), 2.96 (s, 2H), 3.26 (t, J=5.42 Hz, 2H), 3.60 (s, 2H), 7.19 (d, J=8.39 Hz, 1H), 7.42 (d, J=5.19 Hz, 1H), 7.46 (m, 3H), 7.51 (dd, J=7.93, 4.73 Hz, 1H), 7.91 (d, J=8.09,1H), 8.06 (s, 1H), 8.47 (m, 1H), 8.50 (d, J=5.04 Hz, 1H), 8.67 (dd, J=4.73, 1.53 Hz, 1H), 8.99 (s, 1H), 9.26 (d, J=1.98 Hz, 1H) and 10.18 (s, 1H).

4-[(3-Oxo-1-piperazinyl)methyl]benzoic acid

A mixture of 3-bromomethylbenzoic acid (4.30 g, 20 mmol), piperazin-2-one (2.0 g, 20 mmol) and powdered potassium carbonate (2.76 g, 20 mmol) in methanol (50 mL) is stirred for 17 hours at room temperature. The resulting mixture is filtered and the solvent is evaporated off under reduced pressure to give a residue which is treated with hydrochloric acid (80 mL of 0.25 M) and stirred for 5 min. The precipitated product is filtered, washed with water, dried and recrystallised from methanol to give the title compound as a cream crystalline solid.

Example 7

4-[(4-Methyl-3-oxo-1-piperazinyl)methyl]-N-[4-methyl-3-[[4-(3-Pyridinyl)-2-pyrimidinyl]amino]phenyl]benzamide Utilising the procedure described for Example 6, but employing 4-[(4-methyl-3-oxo-1-piperazinyl)methyl]benzoic acid in place of 4-[(3-oxo-1-piperazinyl)methyl]benzoic acid afforded the title compound as a yellow crystalline solid, m.p. 187-192° C.

$^1$H-NMR (500 MHz, DMSO-$d_6$, δ) 2.21 (s, 3H), 2.55 (t, J=5.34 Hz, 2H), 2.91 (s, 2H), 3.15 (m, 2H), 3.61 (s, 2H), 7.19 (d, J=8.24 Hz, 1H), 7.42 (d, J=5.19 Hz, 1H), 7.46 (t, J=8.01 Hz, 1H), 7.48 (m, 2H), 7.51 (dd, J=7.86, 4.81 Hz, 1H), 7.77 (s, 1H), 7.91 (d, J=8.09 Hz, 2H), 8.07 (s, 1H), 8.47 (d, J=7.94 Hz, 1H), 8.50 (d, J=5.19 Hz, 1H), 8.67 (d, J=3.36 Hz, 1H), 8.99 (s, 1H), 9.27 (s, 1H) and 10.18 (s, 1H).

4-[(4-Methyl-3-oxo-1-piperazinyl)methyl]benzoic acid

Utilising the procedure described for 4-[(3-oxo-1-piperazinyl)methyl]benzoic acid, but employing 1-methylpiperazin-2-one in place of piperazin-2-one afforded the title compound as cream crystalline solid.

Example 8

Tablets containing 100 mg of a compound of formula II, for example one of the compounds of formula II described in the Examples 1-4, are usually prepared in the following composition:

Composition:

| | |
|---|---|
| Active ingredient | 100 mg |
| Crystalline lactose | 240 mg |
| Avicel | 80 mg |
| PVPPXL | 20 mg |
| Aerosil | 2 mg |
| Magnesium stearate | 5 mg |
| | 447 mg |

Preparation: The active substance is mixed with carrier materials and compressed on a tableting machine (Korsch EKO, punch diameter 10 mm).

Avicel is microcrystalline cellulose (FMC, Philadelphia, USA).

PVPPXL is polyvinylpolypyrrolidone, cross-linked (BASF, Germany).

Aerosil is silicon dioxide (Degussa, Germany).

Example 9

Capsules containing 100 mg of a compound of formula II, for example one of the compounds of formula II described in the Examples 1-4, are usually prepared in the following composition:

Composition:

| | |
|---|---|
| Active ingredient | 100 mg |
| Avicel | 200 mg |
| PVPPXL | 15 mg |
| Aerosil | 2 mg |
| Magnesium stearate | 1.5 mg |
| | 318.5 mg |

Preparation: The capsules are prepared by mixing the components and filling the mixture into hard gelatin capsules, size 1.

What is claimed is:

1. A compound of formula I

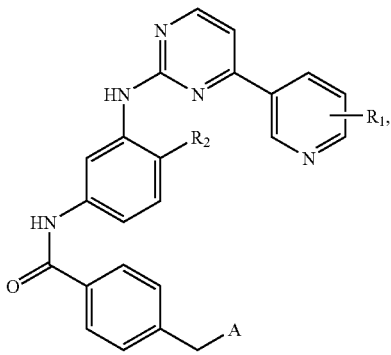
(I)

wherein
$R_1$ is hydrogen or hydroxy,
$R_2$ is hydrogen, lower alkyl or hydroxy-lower alkyl,
A is a piperazinyl group of the formula A'

(A')

substituted by oxo on a ring carbon, and $R_3$ is hydrogen, lower alkyl or acetyl, in purified form or a pharmaceutically acceptable salt of such a compound.

2. A compound selected from the group consisting of 4-[(3-oxo-1-piperazinyl)methyl]-N-[4-methyl-3-[[4-(3-pyridinyl)-2-pyrimidinyl]amino]phenyl]benzamide and 4-[(4-methyl-3-oxo-1-piperazinyl)methyl]-N-[4-methyl-3-[[4-(3-pyridinyl)-2-pyrimidinyl]amino]phenyl]benzamide or a pharmaceutically acceptable salt thereof.

3. A compound which is 4-[(4-methyl-4-oxido-1-piperazinyl)-methyl]-N-{4-methyl-3-[[4-(3-pyridinyl)-2-pyrimidinyl]-amino]-phenyl}-benzamide or a pharmaceutically acceptable salt thereof.

4. A compound which is 4-[(4-methyl-1,4-dioxido-1-piperazinyl)-methyl]-N-{4-methyl-3-[[4-(3-pyridinyl)-2-pyrimidinyl]-amino]-phenyl}-benzamide, or a pharmaceutically acceptable salt thereof.

5. A pharmaceutical composition comprising a compound according to claim 1, or a pharmaceutically acceptable salt thereof, together with a pharmaceutically acceptable carrier.

* * * * *

UNITED STATES PATENT AND TRADEMARK OFFICE
CERTIFICATE OF CORRECTION

| | |
|---|---|
| PATENT NO. | : 7,557,105 B2 |
| APPLICATION NO. | : 10/502291 |
| DATED | : July 7, 2009 |
| INVENTOR(S) | : Börnsen et al. |

It is certified that error appears in the above-identified patent and that said Letters Patent is hereby corrected as shown below:

On the title page delete item "(*) Notice" and insert item --(*) Notice: Subject to any disclaimer, the term of this patent is extended or adjusted under 35 U.S.C. 154(b) by 748 days.--

Signed and Sealed this

Twelfth Day of January, 2010

David J. Kappos
*Director of the United States Patent and Trademark Office*